United States Patent [19]

Starr et al.

[11] Patent Number: 5,543,110
[45] Date of Patent: Aug. 6, 1996

[54] TALL OIL DEODORIZATION PROCESS

[75] Inventors: Fredricke S. Starr, Johns Island; Joseph M. Wong, Mt. Pleasant, both of S.C.; Norman L. Kennedy, Lakeland, Fla.

[73] Assignee: Westvaco Corporation, New York, N.Y.

[21] Appl. No.: 378,474

[22] Filed: Jan. 26, 1995

Related U.S. Application Data

[63] Continuation-in-part of Ser. No. 239,744, May 9, 1994, abandoned, which is a continuation-in-part of Ser. No. 31,826, Mar. 16, 1993, abandoned.

[51] Int. Cl.$^6$ .................................................. A61L 9/015
[52] U.S. Cl. .................. 422/5; 162/51; 530/205; 530/206; 530/218; 530/225
[58] Field of Search .......................... 422/1, 5; 162/16, 162/51; 530/205, 206, 212, 221, 225, 228, 230, 218

[56] References Cited

U.S. PATENT DOCUMENTS

| | | | |
|---|---|---|---|
| 4,970 | 2/1847 | Harman | 530/225 |
| 1,694,179 | 12/1928 | Jenks | 530/228 |
| 2,240,365 | 4/1941 | Dreger | 530/205 |
| 2,275,186 | 3/1942 | Segesseman | 530/205 |
| 2,296,952 | 9/1942 | Ross et al. | 530/205 |
| 2,369,125 | 2/1945 | Anderson | 530/215 |
| 2,419,211 | 4/1947 | Harris . | |
| 2,572,086 | 10/1951 | Wittcoff et al. | 530/217 |
| 2,729,660 | 1/1956 | Harrison | 530/218 |
| 3,423,389 | 9/1969 | Whellus | 530/219 |
| 3,489,740 | 1/1970 | Cholet et al. | 530/206 |
| 3,780,012 | 12/1973 | Smith | 530/218 |
| 4,624,679 | 11/1986 | McEntee | 8/650 |
| 4,725,384 | 2/1988 | DuVernet | 530/218 |
| 4,962,186 | 10/1990 | Johnson, Jr. | 530/218 |
| 5,162,496 | 11/1992 | Johnson, Jr. | 530/212 |

FOREIGN PATENT DOCUMENTS

| | | | |
|---|---|---|---|
| 554699 | 3/1958 | Canada | 162/51 |
| 425243 | 1/1967 | Japan | 162/51 |
| 532866 | 2/1941 | United Kingdom | 530/205 |

*Primary Examiner*—Timothy McMahon
*Attorney, Agent, or Firm*—Terry B. McDaniel; Daniel B. Reece, IV; Richard L. Schmalz

[57] ABSTRACT

A process for deodorizing tall oil rosin and tall oil fatty acids and their derivatives by treating same with an ammonium hydroxide solution under conditions of a steam sparge.

19 Claims, No Drawings

TALL OIL DEODORIZATION PROCESS

This application is a continuation-in-part of application Ser. No. 08/239,744, filed May 9, 1994, now abandoned which is a continuation-in-part of application Ser. No. 08/031,826, filed Mar. 16, 1993, now abandoned.

BACKGROUND OF THE INVENTION

1. Field of the Invention

This invention relates to a method for deodorizing tall oil, to include tall oil fatty acids, tall oil rosin, tan oil fatty acid derivatives, and tall oil rosin derivatives. More particularly, this invention relates to a method for deodorizing esterified tall oil fatty acids and tall oil resin acids. Most particularly, this invention relates to a method for deodorizing tall oil fatty acid and rosin esters with subsequent enhancement and preservation of the odor improvements with certain antioxidants.

2. Description of the Prior Art

Tall oil is derived from a soapy material consisting of the sodium salts of rosin and fatty acids produced, in addition to the desired paper pulp, by the sulfate pulping process. In the primary sulfate pulping process, the kraft process, the fatty acid glycerides are saponified and, along with the free resin acid glycerides also existing in the living pine tree, are converted to sodium soaps. These soap "skimmings," recovered from the kraft black liquor, are convened to crude tall oil (CTO) by reaction with sulfuric acid. The CTO is upgraded by an initial distillation and then is separated into tall oil heads, distilled tall oil, tall oil rosin, and tall oil fatty acids (and/or various fractions of rosin and fatty acids) by subsequent distillations. Throughout the various treatments to which the crude tall oil is subjected, the residual sulfur contaminants from the sulfate pulping process persist in its various products. Often this results in color and odor problems which may limit product applications. This invention method is directed to all of these products of CTO and their derivatives. More particularly, the invention method is directed to esters thereof. Most particularly, the invention method is directed to the pentaerythritol esters of distilled CTO, tall oil heads, rosin, and tall oil fatty acids-primarily to rosin and fatty acid pentaerythritol esters.

Rosin, as a solid resinous material that occurs naturally in the oleoresin of pine trees, may be extracted by means other than tall oil distillation. The three major sources of rosin are: from the oleoresin extrudate of the living pine tree (gum rosin); from the oleoresin contained in the aged stump of the longleaf pine (wood rosin); and from the tall oil produced as a by-product in the kraft paper industry (tall oil rosin). The rosins to which this invention relates include tall oil rosin and derivatives thereof.

Rosin is a complex mixture of mainly $C_{20}$-fused ring, mono-carboxylic acids, typified by levopimaric and abietic acids, and a small amount of nonacidic components. Its color, depending on the source and method of processing, can vary from a very pale yellow through dark red to almost black with a tinge of red. It is generally translucent, brittle at room temperature, and has a slight turpentine odor and taste. It is readily soluble in most organic solvents, such as ethyl alcohol, ethyl ether, mineral spirits, and benzene; it is insoluble in water.

As obtained from its three major sources, rosin is described as "unmodified." The resin acid molecule possesses two chemically reactive centers, the double bonds and the carboxyl group. Reactions at the double bond include isomerization, Diels-Alder and Ene addition reactions, oxidation, hydrogenation, dehydrogenation, and polymerization. Reactions at the carboxyl group include salt formation, esterification, hydrogenolysis, ammonolysis, and decarboxylation. Such reactions, however, are employed to increase the stability and improve the physical properties of rosin, producing "modified rosins."

As stated earlier, the chemical modification of tall oil to which this invention particularly relates is esterification, although it may include esterified fatty and resin acids which also are modified at the double bond. The beneficial product characteristics provided by tall oil fatty acid and rosin esterification for various applications have led to the development of many esterification procedures, particularly treatments with polyhydric alcohols. U.S. Pat. Nos. 2,369,125, 2,590,910, and 2,572,086 (the disclosures of which are incorporated herein by reference) teach rosin esterification with glycerol and pentaerythritol, among other polyhydric alcohols, usually preceded by a rosin disproportionation step.

Rosin ester tackdriers for adhesive products have been used for many years. Traditionally, the tall oil resins have been considered far inferior in odor characteristics to both gum rosin and wood rosin resins. This has been attributed to their high sulfur content due to the chemicals employed in the kraft pulping processes that produce the tall oil-containing black liquor and the elevated temperature history that the tall oil rosin experiences during fractionation of the crude tall oil into fatty and resin acids. Instead of the pleasant "piney" odor of wood or gum rosin, the tall oil rosin exhibits a strongly pungent, burnt quality of odor. As this odor can be carried over into the derivative product and can be intensified by the derivation processing (i.e., esterification at high temperatures), it has limited the use of tall oil rosin derived tackdriers in a number of adhesive areas. Many attempts have been made to improve the odor of tall oil rosin ester tackdriers. Thus, the greatest benefits of this invention are derived when applied to tall oil rosin esters.

Though not specific to tall oil rosin, U.S. Pat. No. 4,970, in 1847, disclosed a method of bleaching rosin by means of alkali, artificial heat, and water, without reporting any effect on odor. U.S. Pat. No. 1,694,179 describes the injection of superheated steam in the vacuum distillation of wood rosin to remove volatile color bodies. Modem tall oil rosin products already having taken advantage of these types of processes are still deficient in odor characteristics.

Likewise, tall oil fatty acid esters produced by traditional esterification techniques possess the latent sulfur or mercaptan odor of the original feedstock, whether it is tall oil heads, distilled tall oil, or tall oil fatty acids. Esterification of tall oil fatty acids is well documented and, with the exception of reaction with methanol, generally can be conducted at atmospheric conditions in an agitated vessel equipped with heating coils and an upright retire condenser. A nitrogen blanket and/or sparging typically is used to protect the product from oxidation, resulting in a product of light color. The product odor, however, can limit application and uses.

For example, the pentaerythritol ester of tall oil fatty acids is known to function as a synthetic lubricant and coolant in the metalworking industry where extreme heat is created due to the friction at the point of contact of the machine tool and the work piece. When the tall oil fatty acid ester is sprayed onto the work piece to alleviate the friction and to reduce the high temperatures, the heat volatilizes the low molecular weight constituents in the metalworking fluid. In addition to agomization of the fluid in the immediate work area due to the high velocity at which the work piece is turned, the volatilization results in furthering the objectionable odor experienced by the workman, whose complaints have limited such use of tall oil fatty acid esters in this application.

Also, unrelated to tall oil rosin, U.S. Pat. No. 4,915,876 discloses a deodorization process for fish oils involving use of mild solutions of acids and/or bases in sequential distillations "to realize highly polyunsaturated oils of enhanced stability."

Purification of wood and gum rosin derived resin is taught by U.S. Pat. No. 2,369,409 to involve mixing with fatty acids, saponifying of the mixture, subjecting the saponified mixture to a strong current of steam or other inert gas, and recoverying (by separating) the resin. This process is complicated and, due to the enhanced odor problems with tall oil rosin, would require multiple treatments, proving uneconomical.

As it is generally known in the art that a significant disadvantage of pentaerythritol esterification of tall oil rosin (as compared with glyerol esterification) is the deterioration of rosin color in the product of the former process, many methods have been developed to improve tall oil rosin pentaerythritol ester color. Some methods teach pre-esterification rosin treatments, such as U.S. Pat. Nos. 3,780,012 and 4,962,186. Other methods teach specific esterification catalysts or catalyst combinations, such as U.S. Pat. Nos. 2,729,660, 3,423,389, 3,780,013, 4,172,070, 4,548,746, 4,725,384, and 4,585,584. None of these teachings, however, suggest rosin ester odor improvements.

The object of the present invention, therefore, is to provide an effective, economical method for deodorizing tall oil rosin and fatty acid ester products and, simultaneously, maintaining or improving product color.

SUMMARY OF THE INVENTION

The object of the present invention is met by the addition of an alkali solution to a sparge treatment of either molten rosin or tall oil fatty acids. The invention process is conveniently employed as a post-esterification steam sparging step of a rosin or tall oil fatty acid esterification process to create a mixture of wet steam and volatile alkali. In a preferred embodiment, the sparging with alkaline steam is conducted in an inert environment and followed by addition of an antioxidant. In a most preferred embodiment of the invention rosin derivative deodorization method, the post-esterification processing includes treatment with activated carbon.

DESCRIPTION OF THE PREFERRED EMBODIMENT(S)

As noted earlier, the primary contributors to offensive odor in tall oil derived fatty acids and rosin are sulfur compounds used in the wood pulping processes of which crude tall oil is a by-product. Therefore, the invention deodorization process may be employed as a final step in a tall oil rosin/fatty acid separation process. Since the consumption of unmodified rosin in the U.S. is insignificant, in the application of the process to rosin it is employed more appropriately as a post-treatment of a tall oil rosin modification procedure, such as esterification of rosin resin acids by reaction of the rosin with an alcohol at elevated temperatures.

The volatile alkali employed in the invention may be selected from the group consisting of ammonium hydroxide, anhydrous ammonia, ethanolamine, morpholine, 2-amino-2-methyl propanol, and trimethylamine. The preferred alkali being ammonium hydroxide.

1. Deodorization of Rosin

A suitable glycerol rosin ester, with low acid number, is produced by heating rosin with glycerol at 250°–290° C. in a vessel provided for the removal of water of esterification. The introduction of catalysts, such as zinc and its salts, provides improvements both in product quality and reduced reaction time. Glycols, such as glycerol and diethylene glycol, also are known to prepare esters by heating rosin at 250°–260° C. in the presence of zinc dust or boric acid catalyst. U.S. Pat. No. 1,820,265 (the disclosure of which is incorporated by reference herein) teaches esterifying rosin with pentaerythritol, erythritol, and anhydroenneaheptitol by heating at 250°–280° C. with a catalyst such as zinc dust or boric acid. The invention process can be applied to rosin esters formed from other alcohols as well. A rosin ester product with a low acid number and a softening point of 95° C. is known to be formed by heating rosin with pentaerythritol 260°–280° C. for seven hours. U.S. Pat. Nos. 4,548,746 and 4,725,384 (the disclosures of which also are incorporated herein by reference) teach as catalysts for tall oil rosin esterification, respectively, the use of phosphinic acid and the combination of phosphinic acid and a phenol sulphide compound while heating the rosin and polyhydric alcohol at 180°–300° C. The post-esterification application of the process of this invention is relevant to all of the above discussed modified rosins, as well as others known and appreciated by those skilled in the art.

Since oxidation is often found to be a primary cause of deterioration in naturally occurring materials, a preferred embodiment of the invention process includes conducting the ammonium hydroxide/steam sparge treatment in an inert environment and/or following said treatment with addition to the rosin of an antioxidant selected from the group consisting of chelating agents, phenolics (such as a hindered bis phenolic marketed as Naugawhite®, an acrylated diphenylamine marketed as Naugawhite® 445, and an alkylated hydroquinone marketed as Naugard® 451), and secondary amines (such as a diphenylamine/acetone reaction product marketed as Aminox®), the last being preferred.

Further odor improvement in the resin esterification product are achieved by subsequent treatment with activated carbon. The rosin ester, in molten state, is combined with activated carbon pellets, and the mixture is agitated sufficiently to suspend the carbon. The carbon/molten ester mixture temperature is held at from about 210° to about 260° C., preferably from about 220° to about 250° C., for from about 2 to about 6 hours, preferably about 4 hours. The carbon can be removed by pressure filtration of the molten ester, preferably using a 0.5 micron Teflon® membrane and a glass prefilter.

Odor evaluations were done both at ambient and elevated temperatures. Ambient temperature evaluations were conducted by passing crushed rosin or modified rosin, which has been treated according to the invention process, through a ¼" mesh screen and collected on a ⅛" mesh screen. A 15 g sample was placed in a 2 oz. glass jar with a secure screwon cap. The odor of such samples can be evaluated after having been tightly closed a minimum of 30 minutes or any designated, controlled time span. Odors were evaluated for intensity and quality against a control.

Intermittent elevated temperature evaluations consisted of placing 1.4–1.5 g of rosin or modified rosin in a small aluminum weighing pan. Preferably, this was a solid flake without fines. The experimental sample was compared directly to a control sample. No more than three samples and the control were evaluated in the same series, and the best samples were duplicated and compared again to the control individually. The aluminum weighing pans were placed, uncovered, on a preheated hot plate (surface temperature= 175° C.±5° C.). The odor was evaluated when the rosin product had completely melted. The surface temperature was increased to 225° C. ±5° C., usually requiring a time span of 5 minutes, and the odor was evaluated again. At this point, volatile matter could be seen clearly evolving from the samples. The pans were removed from the hot plate and allowed to cool. This procedure was repeated with the samples so they would have been evaluated through two elevated temperature cycles. This was done to simulate the compounding of a hot-melt product and its future application. Considering the behavior throughout the two cycles, the samples were rated for intensity and quality.

For both ambient and elevated temperature evaluations, the same descriptor scales were used.

| Descriptor Scales | |
|---|---|
| Intensity | Quality |
| 0. Absent | |
| 1. Perceptible | 1. Bland |
| 2. Very slight | 2. Piney |
| 3. Slight | 3. Tall oil |
| 4. Mild | 4. Burnt tall oil |
| 5. Low | |
| 6. Strong | |
| 7. Severe | |

All deodorized rosin ester samples were tested by the same evaluator in order for the above criteria to be as consistently applied as possible.

The samples subjected to the above described odor evaluations were subjected to the invention deodorization process as set forth above and in the following examples.

EXAMPLE 1(a)

The invention process was employed to deodorize tall oil rosin according to the following procedure:

A 2,000 ml five-neck, round-bottom flask was charged with 1000 g of unmodified rosin, fitted with a mechanical stirrer, nitrogen inlet and outlet, a thermocouple, and a lance delivery system for hot water and ammonium hydroxide addition. The flask was purged with nitrogen and heated slowly (~1.0° C./minute) to the desired treatment temperature (180°–280° C.) under a nitrogen blanket. Agitation was begun as soon as the rosin had melted. Once the desired treatment condition was reached, the molten rosin was nitrogen sparged for one hour, sparged with hot water and ammonium hydroxide for 30 minutes (using a Milton-Roy® minipump with a 46–460 ml/hr. capacity), and hot water for one hour (to simulate steam alone). The treated molten rosin was cooled under a nitrogen blanket to 160°–180° C. and evaluated for odor. While the odor was significantly improved, the rosin color appeared to deteriorate.

EXAMPLE 1(b)

The invention process was employed to deodorize modified rosin which was esterified using the following procedures to simulate a commercial rosin ester marketed as WestRez® 2100:

1. A 2,000 ml reaction flask was charged with 1,000 g unmodified rosin and heated slowly under a nitrogen sparge of 0.0007 lb $N_2$/lb rosin/hour, controlling the "skin" temperature at 200° C. until the rosin liquefied. Upon liquefication, mechanical agitation was begun and heating was continued up to a rosin temperature of 205° C.

2. After the phosphinic acid/phenol sulfide catalyst was added, 142 g of technical grade pentaerythritol (14.2% of the rosin charge) was added.

3. The nitrogen sparge was increased to about 0.002 lb $N_2$ per pound rosin per hour, allowing the liquid temperature to recover and begin heating at about 15° C. per hour until reaching a temperature of from about 260° C. to about 275° C. This temperature is maintained while checking the acid number at least hourly, until the acid number reaches from about 13 to about 15. At this acid number, the nitrogen sparge is increased to about 0.04 lb. $N_2$ per pound of rosin per hour, and the esterified rosin is allowed to begin cooling to about 252° C.

5. At this point the invention process may be employed by introducing hot water/alkali or steam/alkali as far below the surface of the molten rosin ester as possible for the desired time of from about 15 to about 60 minutes, usually 30 minutes, followed by hot water or steam alone for about 30 minutes. After which (at a temperature of about 220° C.) the rosin ester may be neutralized with magnesium acetate and any antioxidant or stabilizer may be added and mixed with the esterified rosin for from about 15 to about 60 minutes, preferably about 45 minutes. After antioxidant addition (or in place thereof) the nitrogen sparge is reduced to 0.002 lb. $N_2$ per pound rosin per hour and the mixture cooled to about 205° C. At this point, determinations of final ester acid number, color, and softening point are made.

A series of rosin esterifications were done according to the above general procedure for comparison with controls not treated as claimed below. The results are shown in the following Table I:

TABLE I

Odor Reduction of Adhesive Tackifiers
Sparging of Un-neutralized Commercial Production Westrez-2100

| Sample Description | Sparge Time | | Aminox conc. | Mag. acet. conc. | Physical Properties | | | Odor Evaluation | |
|---|---|---|---|---|---|---|---|---|---|
| | NH4OH min | steam min | % | % | AN | Color | Soft. Pt. °C. | Ambient | 175–225(° C.) |
| WR-2100 | — | — | — | 0.25 | 9.2 | 4– | 97.5 | low, tall oil | strong, burnt tall oil |

TABLE I-continued

Odor Reduction of Adhesive Tackifiers
Sparging of Un-neutralized Commercial Production Westrez-2100

| Sample Description | Sparge Time NH4OH min | Sparge Time steam min | Aminox conc. % | Mag. acet. conc. % | Physical Properties AN | Color | Soft. Pt. °C. | Odor Evaluation Ambient | Odor Evaluation 175–225(° C.) |
|---|---|---|---|---|---|---|---|---|---|
| 6377-88 | — | 240 0.5 mm Hg | 0 | 0.25 | — | — | 97.2 | low, tall oil | strong, burnt tall oil |
| 6377-69 | 30 | 30 | 0 | 0 | 8.6 | 5 | 97.2 | mild, tall oil | low, tall oil |
| 6377-71 | 60 | 30 | 0 | 0 | — | 4 | 94.4 | low, tall oil | low, tall oil |
| 6377-73 | 30 | 30 | 0 | 0.25 | 8.6 | 4 | 96.7 | very slight, tall oil | slight, tall oil |
| 6377-75 | 30 | 30 | 0.25 | 0 | 9.0 | 5− | 97.8 | Aminox | Aminox |
| 6377-78 | 30 | 30 | 0.10 | 0 | 8.8 | 4+ | 97.8 | very slight, piney | slight, piney |
| 6377-80 | 30 | 30 | 0.10 | 0.25 | 8.0 | 4+ | 98.0 | very slight, piney | slight, piney |
| 6377-82 | 30 | 30 | 0.10 | 0.25 | 7.6 | 4 | 100.0 | very slight, piney | slight, piney |

The reported improvements in odor of the esterified tall oil resins are accompanied by generally maintaining (with minor exceptions) or possibly improving on rosin ester color.

2. Deodorization of Tall Oil Fatty Acids

The odor of low acid number tall oil fatty acid esters produced by traditional esterification means also can be improved by the invention process. As noted with respect to treating rosin esters, the invention process is not considered to be limited according to the alcohol employed in the esterification of the tall oil fatty acid. In particular, those listed above may be used as well as trimetholpropane, neopentyl glycol, and dipentaerythritol.

Typically, esterification involves combining the polyol to tall oil fatty acid in a proportion of 80–85% tall oil fatty acid to 20–15% esterification polyol in the presence of a catalyst such as stannous oxalate in a catalytic amount, preferably 0.1–0.5%, based on total charge weight. The polyol/fatty acid blend is agitated and heated to 220° C. and allowed to react for approximately 8 hours under a nitrogen blanket and/or sparge. The resulting low acid number ester (typically ≦5) can be subjected to deodorization.

The invention deodorization process involves the neutralization of the odoriferous acid components found in tall oil fatty acids and their derivatives with a base which will not interfere with the application properties of the final product. Subsurface atmospheric sparging of the ester with ammonium hydroxide at 150°–200° C., while vigorously agitating the ester has proven successful in reducing the odor of the tall oil fatty acid ester. Subsurface sparging allows intimate contact with the ester and base for neurtalization of the acidic odor components. Furthur benefits (both economic and environmental) may be derived, however, by the subsurface introduction of anhydrous ammonia in a contained reactor vessel under pressures up to 90 psig. This affords containment of the base and enhances its recovery for future reuse. The nitrogen gas also can be recycled from the vapor space of the reactor back into the liquid phase of the product through the subsurface addition port of the reaction vessel.

After the neutralization treatment of the tall oil fatty acid ester has proceeded for 2–4 hours, the product can be steam sparged or steam vacuum sparged to remove the oil or residuals from the ester. While not required, this step can aid in the removal of any residual "ammonia odor."

The final product of the described invention process exhibits improved odor over tall oil fatty acid esters not similarly treated.

Odor evaluations were conducted at both ambient and elevated temperatures. Separate fifteen (15) gram samples of untreated (control) and treated materials were placed in 4 ounce wide mouth polypropylene specimen cups and secured with screw-on caps. Odors were evaluated for intensity and quality against the control.

For both ambient and elevated temperature evaluations, the same descriptor scale were used.

| Descriptor Scale | |
|---|---|
| Intensity | Quality |
| 0. Absent | A. Bland |
| 1. Perceptible | B. Ammoniacal |
| 2. Very slight | C. Tall off fatty acid |
| 3. Slight | D. Tall oil heads |
| 4. Mild | E. Burned |
| 5. Low | F. Sweet |
| 6. Strong | |
| 7. Severe | |

EXAMPLE 2(a)

The invention process was employed to deodorize tall oil fatty acid derivatives according to the following procedure:

To test the commercial viability of the invention, a 1,000 ml three neck, round bottom flask was charged with Westvaco WCC-86B, a commercially available trimethylolpropane (TMP) ester of tall oil fatty acid. The apparatus was fitted with a mechanical stirrer, nitrogen sparge tube, a thermocouple, Dean Stark trap with a water cooled condenser and a subsurface lance for 28% ammonium hydroxide delivery. The fatty acid ester and head space of the flask was degassed with $N_2$ using the subsurface sparge/purge tube. Moderate agitation was commenced at the initial time of heating. Inert gas protection and agitation were continued while heating to 200 ° C. The $N_2$ sparge was used to protect the product from thermal degradation during heating. After reaching 200° C., the $N_2$ sparge was discontinued and the addition of 28% ammonium hydroxide initiated. Fifty (50) ml of ammonium hydroxide were continuously added over 150 minutes. The ammonium hydroxide vapor was collected in the Dean Stark trap equipped with a water cooled condenser. After completion of the ammonium hydroxide addition, the product was sparged subsurface with $N_2$ to remove any residual water and trace odor of ammonia. The product was cooled to ambient conditions where, upon inspection, the product showed no color loss or loss of clarity and exhibited a significantly improved odor. The effectiveness of the invention treatment is indicated in Table II, which shows a comparison between treated and untreated trimethylolpropane fatty acid esters:

TABLE II

| Sample | | Deodorized | Physical Properties | | Odor (Ambient/Elevated) | |
|---|---|---|---|---|---|---|
| Description | Identification | Yes/No | Acid Value | Gardner Color | Intensity | Quality |
| TMP/FA Ester | WCC-86B | No | 9.9 | 13 | 3/5 | C/C, F |
| TMP/FA Ester | 6622-50 | Yes | 9.3 | 12 | 2/3 | C/C, A |

Odor was improved in intensity and in quality, accompanied by a slight improvement in color.

EXAMPLE 2(b)

A 2,000 ml three neck, round bottom flask was simultaneously charged with 1197 grams of distilled tall oil (DTO), 196 grams of trimethylolpropane, and 7 grams stannous oxalate. The apparatus was fitted with a mechanical stirrer, nitrogen sparge tube, a thermocouple, Dean Stark trap with a water cooled condenser. The contents of the reaction flask were degassed with $N_2$ using the subsurface sparge/purge tube. Moderate agitation was commenced at the initial time of heating. Inert gas protection and agitation were continued while heating to 180 ° C. over a period of approximately 45 minutes. The $N_2$ sparge was used to protect the distilled tall oil from thermal degradation during heating. The temperature was increased to 220° C., while continuing the $N_2$ sparge and agitation. The distilled tall oil was esterified to a target acid number of less than 10 over a time period of 5 to 8 hours. After reaching the targeted acid number, the product was allowed to cool to ambient temperature.

A 1,000 ml three neck round bottom flask was charged with 600 grams of the TMP ester of $C_3$ Bottoms distilled tall oil. The apparatus was fitted with a mechanical stirrer, nitrogen sparge tube, a thermocouple, Dean Stark trap with a water cooled condenser and a subsurface lance for 28% ammonium hydroxide delivery. The ester and head space of the flask was degassed with $N_2$ using the subsurface sparge/purge tube. Moderate agitation was commenced at the initial time of heating. Inert gas protection and agitation were continued while heating to 200 ° C. The $N_2$ sparge was used to protect the product from thermal degradation during heating. After reaching 200° C., the $N_2$ sparge was discontinued and the addition of 28% ammonium hydroxide initiated. Fifty (50) ml of ammonium hydroxide were continuously added over 90 minutes. The ammonium hydroxide vapor was collected in the Dean Stark trap equipped with a water cooled condenser. After completion of the ammonium hydroxide addition, the product was sparged subsurface with $N_2$ to remove any residual water and trace odor of ammonia.

The product was cooled to ambient conditions where upon inspection showed no color loss or loss of clarity and exhibited a significantly improved odor over the previously esterified laboratory ester based on distilled tall oil.

TABLE III

| Sample | | Deodorized | Physical Properties | | Odor (Ambient/Elevated) | |
|---|---|---|---|---|---|---|
| Description | Identification | Yes/No | Acid Value | Gardner Color | Intensity | Quality |
| TMP/DTO Ester | 6622-48 | No | 5.0 | 14 | 3.5/5 | C/F, C |
| TMP/DTO Ester | 6622-52 | Yes | 5.3 | 15 | 3/3 | A/F |

Again, the deodorization treatment resulted in improvements in tall oil fatty acid ester odor and color.

EXAMPLE 2(c)

A 2,000 ml three neck, round bottom flask was simultaneously charged with 1197 grams of Westvaco Liqrene A, a commercially available tall oil heads, 196 grams of trimethylolpropane (TMP), and 7 grams stannous oxalate. The apparatus was fitted with a mechanical stirrer, nitrogen sparge tube, a thermocouple, Dean Stark trap with a water cooled condenser. The contents of the reaction flask were degassed with $N_2$ using the subsurface sparge/purge tube. Moderate agitation was commenced at the initial time of heating. Inert gas protection and agitation were continued while heating to 180 ° C. over a period of approximately 45 minutes. The $N_2$ sparge was used to protect the fatty acid heads from thermal degradation during heating. The temperature was increased to 220° C., while continuing the $N_2$ sparge and agitation. The tall oil fatty acid heads were esterified to a target acid number of less than 10 over a time period of 5 to 8 hours. After reaching the targeted acid number, the product was allowed to cool to ambient temperature.

A 1,000 ml three neck, round bottom flask was charged with 600 grams of the TMP ester of Liqrene A. The apparatus was fitted with a mechanical stirrer, nitrogen sparge tube, a thermocouple, Dean Stark trap with a water cooled condenser and a subsurface lance for 28% ammonium hydroxide delivery. The fatty acid ester and head space of the flask were degassed with $N_2$ using the subsurface sparge/purge tube. Moderate agitation was commenced at the initial time of heating. Inert gas protection and agitation were continued while heating to 200 ° C. The $N_2$ sparge was used to protect the product from thermal degradation during heating. After reaching 200° C., the N₂ sparge was discontinued and the addition of 28% ammonium hydroxide initiated. Fifty (50) ml of ammonium hydroxide were continuously added over 90 minutes. The ammonium hydroxide vapor was collected in the Dean Stark trap equipped with a water cooled condenser.

After completion of the ammonium hydroxide addition, the product was sparged subsurface with N₂ to remove any residual water and trace odor of ammonia. The product was cooled to ambient conditions where upon inspection showed no color loss or loss of clarity and exhibited a significantly improved odor over the previously esterified laboratory Liqrene A fatty acid heads ester. Table IV shows a comparison between the treated and untreated tall oil heads fatty acid esters.

TABLE IV

| Sample | | Deodorized | Physical Properties | | Odor (Ambient/Elevated) | |
|---|---|---|---|---|---|---|
| Description | Identification | Yes/No | Acid Value | Gardner Color | Intensity | Quality |
| TMP/Liq. A | 6622-56 | No | 6.3 | 16 | 5/6 | C/D, E |
| TMP/Liq. A | 6622-57 | Yes | 4.6 | 18 | 4/5 | C/D |

In this instance, although there was some color degradation, odor was improved.

It will be understood that it is intended to cover all changes and modifications of the examples of the invention herein chosen for the purpose of illustration which do not constitute departures from the spirit of the invention.

What is claimed is:

1. A process for deodorizing a tall oil comprising the step of treating the tall oil with a volatile alkaline solution under conditions of a stem sparge.

2. The process of claim 1 wherein the tall oil is selected from the group consisting of tall oil rosin and tall oil fatty acid.

3. The process of claim 2 wherein the tall oil rosin is tall oil rosin ester.

4. The process of claim 3 wherein the tall oil rosin ester is the reaction product of the rosin and an alcohol of the group consisting of glycerol, pentaerythritol, erythritol, anhydroenneaheptitol, glycol, and diethylene glycol.

5. The process of claim 1 wherein the volatile alkaline solution is selected from a member of solutions prepared with ammonium hydroxide, anhydrous ammonia, ethanolamine, morpholine, 2-amino-2-methyl propanol, and trimethylamine.

6. The process of claim 5 wherein the volatile alkaline solution is prepared with ammonium hydroxide.

7. The process of claim 1 further comprising the step of adding an antioxidant to the treated tall oil.

8. The process of claim 7 wherein the antioxidant is selected from the group consisting of chelating agents, phenolics, and secondary amines.

9. The process of claim 8 wherein the antioxidant is a phenolic compound selected from the group consisting of a hindered bis phenolic, an acrylated diphenylamine, and an alkylated hydroquinone.

10. The process of claim 9 wherein the antioxidant is the secondary amine produced by the reaction between diphenylamine and acetone.

11. The process of claim 4 wherein magnesium acetate is subsequently added to neutralize the rosin ester.

12. The process of claim 1 wherein the treatment is conducted in an inert atmosphere.

13. The process of claim 3 further comprising treatment of the rosin ester, in molten form, with activated carbon from about 2 to about 6 hours at about 210° to about 260° C., and separating the rosin ester from the carbon by filtration.

14. The process of claim 13 wherein the rosin ester is combined with the activated carbon for about 4 hours at about 220° to about 250° C.

15. The process of claim 13 wherein the filtration of the molten rosin ester is accomplished under pressure utilizing 0.5 micron membrane and a glass prefilter.

16. The process of claim 2 wherein the tall oil fatty acid is a tall oil fatty acid ester.

17. The process of claim 16 wherein the tall oil fatty acid ester is derived from a member of the group consisting of tall oil, tall oil heads, distilled tall oil, and tall oil fatty acid.

18. The process of claim 17 wherein the tall oil fatty acid ester is prepared with an alcohol of the group consisting of glycerol, pentaerythritol, anhydroenneaheptitol, glycol, trimetholpropane, neopentyl glycol, dipentaerythritol, and diethylene glycol.

19. The process of claim 15 wherein the volatile alkaline solution is selected from a member of solutions prepared with ammonium hydroxide, anhydrous ammonia, ethanolamine, morpholine, 2-amino-2-methyl propanol, and trimethylamine.

* * * * *